(12) United States Patent
Kitajima et al.

(10) Patent No.: US 8,779,010 B2
(45) Date of Patent: Jul. 15, 2014

(54) WATER-IN-OIL EMULSIFIED COSMETIC

(75) Inventors: Masaki Kitajima, Yokohama (JP); Ayako Ibe, Yokohama (JP); Kei Watanabe, Yokohama (JP); Takayuki Omura, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 14/007,731

(22) PCT Filed: Mar. 29, 2012

(86) PCT No.: PCT/JP2012/058435
§ 371 (c)(1),
(2), (4) Date: Sep. 26, 2013

(87) PCT Pub. No.: WO2012/133686
PCT Pub. Date: Oct. 4, 2012

(65) Prior Publication Data
US 2014/0018444 A1    Jan. 16, 2014

(30) Foreign Application Priority Data
Mar. 30, 2011 (JP) .................. 2011-074419

(51) Int. Cl.
*A61K 47/00* (2006.01)
(52) U.S. Cl.
USPC ........................................................ 514/785
(58) Field of Classification Search
None
See application file for complete search history.

(56) References Cited

U.S. PATENT DOCUMENTS

2007/0274932 A1* 11/2007 Suginaka et al. ............... 424/59

FOREIGN PATENT DOCUMENTS

| JP | 56-040605 | | 4/1981 |
|---|---|---|---|
| JP | 10-001413 | | 1/1998 |
| JP | 10001413 B | * | 1/1998 |
| JP | 2004-059530 | | 2/2004 |
| JP | 2005-306797 | | 11/2005 |
| JP | 2007-204377 | | 8/2007 |
| JP | 2007204377 | * | 8/2007 |
| JP | 2010-215525 | | 9/2010 |
| JP | 2010-229103 | | 10/2010 |

OTHER PUBLICATIONS

Patent Abstracts of Japan, Publication No. 2004-059530, 9 pages, Feb. 26, 2004.
Patent Abstracts of Japan, Publication No. 56-040605, 1 page, Sep. 11, 1979.
Patent Abstracts of Japan, Publication No. 2007-204377, 11 pages, Jan. 31, 2006.
Patent Abstracts of Japan, Publication No. 10-001413, 14 pages, Jan. 6, 1998.
Patent Abstracts of Japan, Publication No. 2010-215525, 10 pages, Sep. 30, 2010.
Patent Abstracts of Japan, Publication No. 2005-306797, 10 pages, Nov. 4, 2005.
Patent Abstracts of Japan, Publication No. 2010-229103, 15 pages, Oct. 14, 2010.

* cited by examiner

*Primary Examiner* — Wu-Cheng Winston Shen
*Assistant Examiner* — Jean Cornet
(74) *Attorney, Agent, or Firm* — Rankin, Hill & Clark LLP

(57) ABSTRACT

The present invention provides a water-in-oil emulsion cosmetic that is excellent in the resilient and supple (in other words, firm and tensional) feels and also excellent in the moisturizing effect and feeling in use. The water-in-oil emulsion cosmetic of the present invention is characterized by comprising the following (A) to (D):
(A) 0.5 to 10 mass % of bis-diglyceryl polyacyladipate-2
(B) an oil containing (b1)
(b1) a volatile oil of low compatibility with (A)
(C) an emulsifying agent
and (D) 60 to 90 mass % of an aqueous component,
wherein the percentage of component (b1) is 40 to 85% with respect to component (A) and component (B).

2 Claims, 3 Drawing Sheets

WATER-IN-OIL EMULSIFIED COSMETIC

RELATED APPLICATIONS

This application claims the priority of Japanese Patent Application No. 2011-74419 filed on Mar. 30, 2011, which is incorporated herein by reference.

FIELD OF THE INVENTION

The present invention relates to an water-in-oil emulsion cosmetic, and in particular, relates to the water-in-oil emulsion cosmetic that is excellent in the resilient and supple (in other words, firm and tensional) feels and also excellent in the moisturizing effect and feeling in use.

BACKGROUND OF THE INVENTION

An emulsion is broadly-divided into an oil-in-water (O/W) type and a water-in-oil (W/O) type. In addition to these types, there are multi-type emulsions such as oil-in-water-in-oil (O/W/O) type and water-in-oil-in-water (W/O/W) type. Conventionally, these emulsions have been utilized in a skin-care cream, a milky lotion, and a hair-care cream, etc in the cosmetic field.

Among them, a water-in-oil emulsion cosmetic, in which an oil phase constitutes the outer phase and a water phase constitutes the inner phase, is a suitable form as a cosmetic because oil-soluble active ingredients such as an emollient oil, an oil-soluble drug, and a UV absorber can be efficiently spread on the skin. In this regard, a water-in-oil emulsion is superior to an oil-in-water emulsion.

In recent years, it is desired for such water-in-oil emulsion cosmetics to impart a resilient and supple feels to the skin (feeling in use wherein the skin does not sag, is not taut, and has moderate elasticity).

In the past, as the material that imparts a resilient and supple feels, polymers and the like have been used. For example, water-in-oil emulsion compositions that have a resilient and supple feels by the use of polyaspartic acid salts (patent literature 1) or polyvinyl alcohol (patent literature 2) are known.

However, the resilient and supple feels sometimes become weak owing to the moisturizer and oil that are blended to generate a moisturizing effect and other feeling in use.

Patent literature 1: Japanese unexamined patent publication No. 2005-306797
Patent literature 2: Japanese unexamined patent publication No. 2010-229103

DISCLOSURE OF THE INVENTION

Problem to be Solved by the Invention

The present invention was made in view of the above-described problems of the conventional art. An object of the invention is to provide a water-in-oil emulsion cosmetic that is excellent in the resilient and supple feels and moisturizing effect.

Means to Solve the Problem

The present inventors have diligently studied to solve the above-described problem. As a result, the present inventors have found that both a resilient/supple feel and moisturizing effect can be achieved in the water-in-oil emulsion cosmetic that is prepared by blending bis-diglyceryl polyacyladipate-2 and a volatile oil of low compatibility with bis-diglyceryl polyacyladipate-2, thus completing the present invention.

That is, the water-in-oil emulsion cosmetic of the present invention is characterized by comprising the following (A) to (D):
(A) 0.5 to 10 mass % of bis-diglyceryl polyacyladipate-2
(B) an oil containing (b1)
(b1) a volatile oil of low compatibility with (A)
(C) an emulsifying agent
and (D) 60 to 90 mass % of an aqueous component,
wherein the percentage of component (b1) is 40 to 85% with respect to component (A) and component (B).

In the water-in-oil emulsion cosmetic, it is preferable that (b2) an oil with a viscosity less than 1000 mPa·s is contained in component (B), and the blending quantity of component (b2) is two times or less of the blending quantity of component (A).

Effect of the Invention

The water-in-oil emulsion cosmetic of the present invention is a cosmetic comprising bis-diglyceryl polyacyladipate-2, an oil containing a volatile oil of low compatibility with bis-diglyceryl polyacyladipate-2, an emulsifying agent, and an aqueous component; thus a water-in-oil emulsion cosmetic excellent in the resilient and supple feels and also excellent in the moisturizing effect and feeling in use can be provided.

BEST MODE FOR CARRYING OUT THE INVENTION

Figure 1:
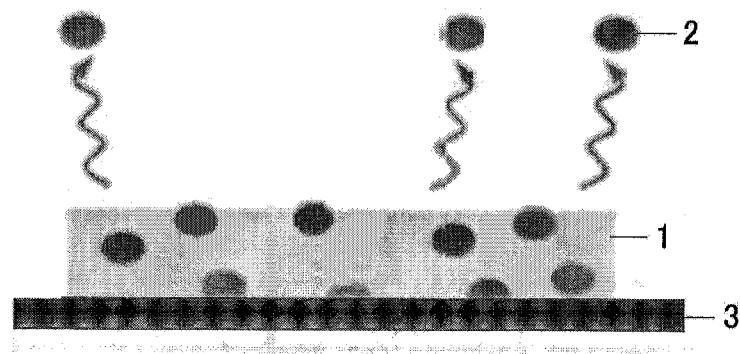
FIG. 1 shows the behavior of bis-diglyceryl polyacyladipate-2 and the additional oil (volatile oil highly compatible with bis-diglyceryl polyacyladipate-2) on the skin.

A water-in-oil emulsion cosmetic of the present invention contains (A) bis-diglyceryl polyacyladipate-2, (B) (b1) an oil containing a volatile oil of low compatibility with bis-diglyceryl polyacyladipate-2, (C) an emulsifying agents, and (D) an aqueous component.

In the following, each component is described in detail.

(A) Bis-diglyceryl polyacyladipate-2

Bis-diglyceryl polyacyladipate-2 is ester oil of diglycerol with adipic acid, octanoic acid, decanoic acid, isostearic acid, stearic acid, and hydroxystearic acid.

As a commercial bis-diglyceryl polyacyladipate-2, Softisan 649 (manufactured by Sasol) can be listed.

It is necessary that the blending quantity of (A) bis-diglyceryl polyacyladipate-2 of the water-in-oil emulsion cosmetic of the present invention is 0.5 to 10 mass % with respect to the total amount of the cosmetic. The blending quantity of component (A) is preferably 1 mass % or higher. If it is less than 0.5 mass %, the satisfactory resilient and supple feels and moisturizing effect cannot be obtained. The blending quantity of component (A) is preferably 5 mass % or lower. If it exceeds 10 mass %, the feeling in use such as non-stickiness or softness and stability are poor.

(B) Oil

In the (B) oil in the present invention, it is necessary to contain component (b1), namely, a volatile oil of low compatibility with (A) bis-diglyceryl polyacyladipate-2.

Here, the oil of low compatibility with bis-diglyceryl polyacyladipate-2 is the oil wherein when bis-diglyceryl polyacyladipate-2 and the subject oil are mixed, heated to 80° C., and cooled to room temperature; a uniform transparent layer is not formed. The volatile oil means the oil whose boiling point is 300° C. or lower at 1 atmosphere.

Examples of such components (b1) include hexamethylcyclotrisiloxane, octamethylcyclotetrasiloxane, decamethylcyclopentasiloxane, dodecamethylcyclohexasiloxane, hexamethyldisiloxane, octamethyltrisiloxane, decamethyltetrasiloxane, dodecamethylpentasiloxane, tetradecamethylhexasiloxane, hexadecamethylheptasiloxane, methyltris(trimethylsiloxy) silane, tetrakis(trimethylsiloxy) silane, perfluoromethyl cyclopentane, perfluorodimethyl cyclohexane, methylperfluoro butyl ether, methylperfluoro isobutyl ether, ethylperfluoro butyl ether, and ethylperfluoro isobutyl ether.

In the water-in-oil emulsion cosmetic of the present invention, the blending quantity of (b1), the volatile oil of low compatibility with bis-diglyceryl polyacyladipate-2, is preferably 6 mass % or higher with respect to the total amount of the cosmetic, more preferably 10 mass % or higher, and especially preferably 13 mass % or higher. If the blending quantity is too small, the resilient and supple feels may be poor. The blending quantity of component (b1) is preferably 20 mass % or lower and especially preferably 18 mass % or lower. If the blending quantity is too large, the feeling in use may be poor.

In the water-in-oil emulsion cosmetic of the present invention, it is preferable to blend (b2) an oil whose viscosity is less than 1000 mPa·s in addition to component (b1), which is the above-described essential component in the (B) oil. In the present invention, viscosity is a value measured with a viscometer at ordinary temperature (25° C.) (measurement conditions with the viscometer: BL-type, 12 rpm, rotor No. 2).

Examples of such (b2) oils whose viscosities are less than 1000 mPa·s include silicone oils, polar oils, and nonpolar oils.

Examples of silicone oils include linear silicone oils such as dimethylpolysiloxane, methylphenyl polysiloxane, and methylhydrogen polysiloxane, and cyclic silicone oils.

Examples of polar oils include ester oils such as cetyl octanoate, hexyl laurate, isopropyl myristate, octyl palmitate, isocetyl stearate, isopropyl isostearate, octyl isopalmitate, isodecyl iso stearate, 2-ethylhexyl succinate, and diethyl sebacate.

Examples of nonpolar oils include hydrocarbon oils such as liquid paraffin, squalane, squalene, paraffin, and isohexadecane.

When component (b2) is blended into the water-in-oil emulsion cosmetic of the present invention, it is preferable that the blending quantity of component (b2) is two times or less of the blending quantity of component (A). If the blending quantity of component (b2) exceeds two times of the blending quantity of component (A), the satisfactory resilient and supple feels may not be obtained.

In the cosmetic of the present invention, it is also preferable to additionally blend (b3) a high-viscosity oil.

In the present invention, (b3) the high-viscosity oil means an oil selected from the group consisting of solid oils, semisolid oils except for component (A), and oils with a viscosity of 1000 mPa·s or higher. These oils may be blended either alone or in combination of two or more.

Because of the presence of the high-viscosity oil, water-in-oil emulsion cosmetics excellent in the resilient and supple feels and moisturizing effect can be obtained. In the present invention, the blending quantity of the high-viscosity oil does not affect the stability of emulsion cosmetics.

Among (b3) high-viscosity oils, examples of solid oils include solid fats such as cacao butter, coconut oil, horse fat, hydrogenated coconut oil, palm oil, beef fat, mutton suet, and hydrogenated castor oil, hydrocarbons such as paraffin wax (linear hydrocarbon), microcrystalline wax (branched saturated hydrocarbon), ceresin wax, Japan wax, and Fischer-Tropsch wax, waxes such as beeswax, carnauba wax, candelilla wax, rice bran wax (rice wax), spermaceti, jojoba oil, insect wax, montan wax, kapok wax, bayberry wax, shellac wax, sugarcane wax, lanolin fatty acid isopropyl, hexyl laurate, reduced lanolin, hard lanolin, POE lanolin alcohol ether, POE lanolin alcohol acetate, POE cholesterol ether, lanolin fatty acid polyethylene glycol, and POE hydrogenated lanolin alcohol ether, higher fatty acids such as myristic acid, palmitic acid, stearic acid, and behenic acid, and higher alcohols such as cetyl alcohol, stearyl alcohol, behenyl alcohol, myristyl alcohol, and cetostearyl alcohol.

Examples of semisolid oils except for component (A) include plant oils such as vaseline, lanolin, shea butter, and partial hydrogenated coconut oil, partial hydrogenated jojoba oil, pentaerythrityl tetra(behenate/benzoate/ethylhexanoate), macadamia seed oil polyglyceryl-6 esters behenate, (phytosteryl/behenyl) dimer dilinoleate, and dipentaerythrityl hexaoxystearate.

As oils with a viscosity of 1000 mPa·s or higher except for component (A), the examples include glyceryl triisostearate, diisostearyl malate, hydrogenated lanolin, and hydrogenated polyisobutene.

In the outer phase (oil phase) of the water-in-oil emulsion cosmetic of the present invention, it is preferable that (A) bis-diglyceryl polyacyladipate-2 is dispersed in the continuous-phase component (b1).

Although component (A) has low compatibility with component (b1), component (A) does not separate in component (b1) and a stable fine dispersion can be achieved in the emulsion cosmetic of the present invention, in which the blending quantity of the inner water phase is large as described above.

In the water-in-oil emulsion cosmetic, it is necessary that the percentage of component (b1) is 40 to 85% with respect to component (A) and component (B). The percentage of component (b1) is preferably 55 to 85% with respect to component (A) and component (B). If the percentage of component (b1) is 40% or lower with respect to component (A) and component (B), the satisfactory resilient and supple feels may not be obtained. If it exceeds 85%, the stability and feeling in use may be poor.

(C) Emulsifying Agent

As the (C) emulsifying agent, those normally usable in cosmetics can be used.

It is especially preferable to use a surfactant whose HLB is 5 or lower. If the HLB exceeds 5, the hydrophilicity is high and it may be difficult to obtain a stable water-in-oil emulsion cosmetic.

The above HLB value can be calculated by Kawakami's equation, which is expressed by $HLB = 7 + 11.7 \cdot \log(MW/MO)$ (here, MW represents the molecular weight of the hydrophilic group, and MO represents the molecular weight of the lipophilic group).

Examples of such surfactants include organic modified clay mineral, silicone-type surfactant, and polyol fatty acid ester surfactant.

Examples of organic modified clay minerals include dimethyl alkyl ammonium hectorite, benzyl dimethyl stearyl ammonium hectorite, and stearyl dimethyl ammonium chloride-treated alminium magnesium silicate.

Examples of silicone-type surfactants include poly(oxyethylene/oxypropylene) methyl polysiloxane copolymer, polyoxyethylene methylpolysiloxane copolymer, silicone chain branched-type methyl polysiloxane copolymer, alkyl chain branched-type polyoxyethylene methyl polysiloxane copolymer, alkyl chain/silicone chain branched-type polyoxyethylene methyl polysiloxane copolymer, crosslinked-type polyoxyethylene methyl polysiloxane, crosslinked-type comprising an alkyl group polyoxyethylene methyl polysiloxane, branched-type polyglycerin modified silicone, crosslinked-type polyglycerin modified silicone, crosslinked-type comprising an alkyl group polyglycerin modified silicone, and alkyl chain branched-type polyglycerin modified silicone.

Examples of polyol fatty acid ester surfactants include glyceryl fatty acid ester, polyglyceryl fatty acid ester, polyoxyethylene glyceryl fatty acid ester, sorbitan fatty acid ester, and polyoxyethylene sorbitan fatty acid ester.

The blending quantity of (C) emulsifying agent of the water-in-oil emulsion cosmetic of the present invention is preferably 0.5 mass % or higher with respect to the total amount of the cosmetic, especially preferably 1 mass % or higher. If it is too small, the stability may be poor. The blending quantity of component (C) is preferably 5 mass % or lower with respect to the total amount of the cosmetic, especially preferably 4 mass or lower. If it is too large, the feeling in use may be poor.

(D) Aqueous Component

The (D) aqueous component, which can be normally used for cosmetics, can be blended so far as it does not deteriorate emulsion stability.

Examples of such (D) aqueous components include moisturizer, water-soluble polymer, UV absorber, sequestering agent, antioxidant, and drug.

Examples of moisturizers include 1,3-butylene glycol, polyethylene glycol, propylene glycol, dipropylene glycol, hexylene glycol, glycerin, diglycerin, xylitol, maltitol, maltose, and D-mannite Examples of water-soluble polymers include plant-based polymers such as gum arabic, carrageenan, pectine, agar, quince seed (marmelo), starch, and algae colloid (brown algae extract), microorganism-based polymers such as dextran and pullulan, animal-based polymers such as collagen, casein, and gelatine, starch-based polymers such as carboxymethyl starch and methylhydroxypropyl starch, alginic acid-based polymers such as sodium alginate, vinyl-based polymers such as carboxy vinyl polymer (e.g., CARBOPOL®), polyoxyethylene-based polymers, polyoxyethylene/polyoxypropylene copolymer-based polymers, acryl-based polymers such as sodium polyacrylate and polyacrylamide, and inorganic-based water-soluble polymers such as bentonite, magnesium aluminium silicate, and laponite.

Examples of UV absorbers include benzoic acid-based UV absorbers such as p-aminobenzoic acid, anthranilic acid-based UV absorbers such as methyl anthranilate, salicylic acid-based UV absorbers such as octyl salicylate and phenyl salicylate, cinnamic acid-based UV absorbers such as isopropyl p-methoxycinnamate, octyl p-methoxycinnamate, and glyceryl mono-2-ethylhexanoate di-p-methoxycinnamate, benzophenone-based UV absorbers such as 2,4-dihydroxybenzophenone, 2-hydroxy-4-methoxybenzophenone, and 2-hydroxy-4-methoxybenzophenone-5-sulfonic acid, urocanic acid, 2-(2'-hydroxy-5'-methylphenyl)benzotriazole, and 4-tert-butyl-4'-methoxybenzoylmethane.

Examples of sequestering agents include sodium edetate, sodium metaphosphate, and phosphoric acid.

Examples of antioxidants include ascorbic acid, alpha-tocopherol, dibutylhydroxytoluene, and butylhydroxyanisole.

Examples of drugs include vitamins such as vitamin A oil, retinol, retinol palmitate, inositol, pyridoxine hydrochloride, benzyl nicotinate, nicotinamide, dl-alpha-tocopherol nicotinate, magnesium ascorbyl phosphate, ascorbic acid 2-glucoside, vitamin D2 (ergocalciferol), L-ascorbic acid dl-alpha-tocopherol phosphoric acid diester potassium salt, dl-alpha-tocopherol, dl-alpha-tocopheryl acetate, pantothenic acid, and biotin, anti-inflammatory agents such as allantoin and azulene, whitening agents such as arbutin, 4-methoxy salicylate or its salt, and tranexamic acid or its derivative, astringent agents such as zinc oxide and tannic acid, sulfur, lysozyme chloride, pyridoxine hydrochloride, and gamma-orizanol.

The above-mentioned drugs can be used in a free state, a form of acid or basic salt if one can become salts, or a form of ester if one has a carboxylic acid group.

It is necessary that the blending quantity of (D) aqueous component of the water-in-oil emulsion cosmetic of the present invention is 60 to 90 mass % with respect to the total amount of the cosmetic. The blending quantity of component (D) is preferably 65 mass % or higher. If it is less than 60 mass %, the separation or precipitation of bis-diglyceryl polyacyladipate-2 may take place, or the feeling in use of cosmetics is poor. The blending quantity of component (D) is preferably 85 mass % or lower. If it exceeds 90 mass %, the stability is poor.

The water-in-oil emulsion cosmetic of the present invention can be widely applied for cosmetics which are commonly applied to the skin, and the examples include products such as a whitening essence, a milky lotion, a cream, a pack, a foundation, a lipstick, an eye shadow, a eyeliner, a mascara, a face wash, a spray, a mouse, a hair rinse, and a shampoo.

EXAMPLES

The present invention will be further described in the following examples, however, the invention is not limited by these examples. Unless otherwise specified, the blending quantity will be represented as mass % with respect to a system in which each component is blended.

Prior to illustrating the examples, the evaluation methods for the tests used in the present invention will be explained.

Evaluation (1): Dispersion Stability

The sample appearance was visually evaluated one week after preparation.

A: Separation of oil was not observed.
B: Oil separated and precipitation was observed.
C: Within in one week, oil separated and precipitation was observed.

Evaluation (2): Resilient and Supple (in other Words, Firm and Tensional) Feel 10 professional panelists applied each of the samples to face and evaluated the feeling in use upon application.

A*: Among 10 professional panelists, 9 or more panelists answered that the resilient and supple feels were present.
A: Among 10 professional panelists, 7 or more and less than 9 panelists answered that the resilient and supple feels were present.
B: Among 10 professional panelists, 5 or more and less than 7 panelists answered that the resilient and supple feels were present.

C: Among 10 professional panelists, less than 5 panelists answered that the resilient and supple feels were present.

Evaluation (3): Stability

The stability was evaluated by comparing the hardness and appearance of a sample stored for 1 month at 25° C. and 40° C. with those of a sample immediately after the preparation.

A*: Under all storage conditions, the decrease of hardness was 10% or less, and no change in appearance was observed.

A: Under all storage conditions, no change in appearance was observed, however, the decrease of hardness of 10% or higher was observed only for the sample stored at 40° C.

B*: Under all storage conditions, no change in appearance was observed, however, the decrease of hardness of 10% or higher was observed.

B: The separation of water or oil was slightly observed in the appearance.

C: Within 1 month, the separation of water or oil was observed in the appearance.

Evaluation (4): Elastic Feeling 10 professional panelists applied each of the samples to face and evaluated the feeling in use upon application.

A*: Among 10 professional panelists, 9 or more panelists answered that the elastic feeling was present.

A: Among 10 professional panelists, 7 or more and less than 9 panelists answered that the elastic feeling was present.

B: Among 10 professional panelists, 5 or more and less than 7 panelists answered that the elastic feeling was present.

C: Among 10 professional panelists, less than 5 panelists answered that the elastic feeling was present.

Evaluation (5): Softness 10 professional panelists applied each of the samples to face and evaluated the feeling in use upon application.

A*: Among 10 professional panelists, 9 or more panelists answered that the skin was soft.

A: Among 10 professional panelists, 7 or more and less than 9 panelists answered that the skin was soft.

B: Among 10 professional panelists, 5 or more and less than 7 panelists answered that the skin was soft.

C: Among 10 professional panelists, less than 5 panelists answered that the skin was soft.

Evaluation (6): Moisturizing Effect 10 professional panelists applied each of the samples to face and evaluated the feeling in use upon application.

A*: Among 10 professional panelists, 9 or more panelists answered that the moisturizing effect was present.

A: Among 10 professional panelists, 7 or more and less than 9 panelists answered that the moisturizing effect was present.

B: Among 10 professional panelists, 5 or more and less than 7 panelists answered that the moisturizing effect was present.

C: Among 10 professional panelists, less than 5 panelists answered that the moisturizing effect was present.

The present inventors investigated the resilient and supple feels by using bis-diglyceryl polyacyladipate-2 (Softisan 649 (manufactured by Sasol) as the polymer that has high adhesion to the skin and provides resilient and supple feels. Bis-diglyceryl polyacyladipate-2 is semi-solid form at ordinary temperature (melting point: about 40° C. (dropping point: 32 to 33° C.)); therefore, it is difficult to blend bis-diglyceryl polyacyladipate-2 alone in cosmetics.

Accordingly, the cosmetics in which bis-diglyceryl polyacyladipate-2 and various additional oils were blended were produced as shown in Table 1 below. Then, each sample was evaluated for the evaluation items (1) and (2) in the above-described evaluation criteria. The results are shown in Table 1.

In the following tests, "compatibility (*1)" means the compatibility of bis-diglyceryl polyacyladipate-2 with the additional oil. That is, when the two kinds of oil, namely, bis-diglyceryl polyacyladipate-2 and the additional oil were mixed, heated to 80° C., and cooled to room temperature; "o" if a uniform transparent layer was formed and "x" if a uniform transparent layer was not formed.

TABLE 1

| | Compatibility(*1) | Property | Test Example | | | | |
| --- | --- | --- | --- | --- | --- | --- | --- |
| | | | 1-1 | 1-2 | 1-3 | 1-4 | 1-5 |
| Bis-diglyceryl polyacyladipate-2 | | | 50 | 50 | 50 | 50 | 50 |
| Isohexadecane | O | volatile | 50 | — | — | — | — |
| Squalane | O | non-volatile | — | 50 | — | — | — |
| Decamethylcyclopentasiloxane | X | volatile | — | — | 50 | — | — |
| Decamethyltetrasiloxane | X | volatile | — | — | — | 50 | — |
| Dimethylpolysiloxane 6 cs | X | non-volatile | — | — | — | — | 50 |
| Evaluation (1): Dispersion stability | | | A | A | C | C | C |
| Evaluation (2): Resilient and supple feels | | | C | C | A | A | C |

The oil-based cosmetics of Test Examples 1-1 and 1-2 containing the oil (isohexadecane or squalane), which is normally blended with bis-diglyceryl polyacyladipate-2 and can dissolve the semi-solid oil (bis-diglyceryl polyacyladipate-2), were stable; however, there was no resilient and supple feels.

In Test Examples 1-3 to 1-5, wherein bis-diglyceryl polyacyladipate-2 and an oil of low compatibility with bis-diglyceryl polyacyladipate-2 (decamethylcyclopentasiloxane, decamethyltetrasiloxane, or dimethylpolysiloxane) were blended, the bis-diglyceryl polyacyladipate-2 precipitated over time and the stability was poor. However, the samples of Test Examples 1-3 and 1-4, in which a volatile oil was blended, were excellent in resilient and supple feels.

The present inventors investigated the behavior, on the skin, of the oil in the cosmetic (bis-diglyceryl polyacyladipate-2), which achieves a resilient/supple feel, and the behavior of the additional oil blended therewith. The results are shown in FIGS. 1 to 3.

As in Test Example 1-1, when the volatile oil (isohexadecane) highly compatible with bis-diglyceryl polyacyladipate-2 was used as the additional oil, we considered that the behavior shown in FIG. 1 is displayed. That is, because isohexadecane is highly compatible with bis-diglyceryl polyacyladipate-2, it is considered that a part evaporates and a part coexists, and a low concentration of bis-diglyceryl polyacyladipate-2 is coated on the skin.

Figure 2:
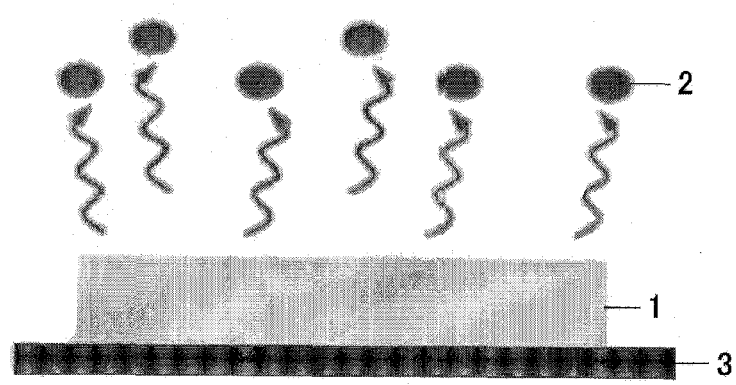
FIG. 2 shows the behavior of bis-diglyceryl polyacyladipate-2 and the additional oil (volatile oil low compatible with bis-diglyceryl polyacyladipate-2) on the skin.

As in Test Example 1-3, when the volatile oil (decamethylcyclopentasiloxane) of low compatibility with bis-diglyceryl polyacyladipate-2 was used as the additional oil, we considered that the behavior shown in FIG. 2 is displayed. That is, because decamethylcyclopentasiloxane is of low compatibility with bis-diglyceryl polyacyladipate-2, the volatile oil decamethylcyclopentasiloxane instantly separates and easily evaporates when the cosmetic is applied on the skin. Accordingly, a large amount of bis-diglyceryl polyacyladipate-2 is considered to adhere on the skin As in Test Example 1-5, when a non-volatile oil (dimethylpolysiloxane) of low compatibility with bis-diglyceryl polyacyladipate-2 was used as the additional oil, we considered that the behavior shown in FIG. 3 is displayed. That is, because dimethylpolysiloxane is of low compatibility with bis-diglyceryl polyacyladipate-2 and non-volatile, bis-diglyceryl polyacyladipate-2 and dimethylpolysiloxane are non-uniform when the cosmetic is applied on the skin. Thus, it is considered that each of them separately aggregates and adheres to the skin and unevenness is caused.

Figure 3:
FIG. 3 shows the behavior of bis-diglyceryl polyacyladipate-2 and the additional oil (non-volatile oil low compatible with bis-diglyceryl polyacyladipate-2) on the skin.

From Table 1 and FIGS. 1 to 3, it is considered that the properties of adhesion and rubbing to the skin of bis-diglyceryl polyacyladipate-2 are achieved in the system wherein a large amount of bis-diglyceryl polyacyladipate-2 adheres to the skin when the cosmetic is applied on the skin, and cosmetics excellent in resilient and supple feels can be obtained.

Thus, it was found, as in Test Examples 1-3 and 1-4, that the elasticity effect of bis-diglyceryl polyacyladipate-2 can be maximized by using bis-diglyceryl polyacyladipate-2 in combination with a volatile oil of low compatibility with bis-diglyceryl polyacyladipate-2.

However, when bis-diglyceryl polyacyladipate-2 and a volatile oil of low compatibility with bis-diglyceryl polyacyladipate-2 were blended, a cosmetic satisfactory in stability could not be obtained as described above.

Therefore, the present inventors blended these oils into water-in-oil emulsion cosmetics and tried to suppress the separation of bis-diglyceryl polyacyladipate-2 in the oil phase.

That is, the present inventors produced, by the conventional method, water-in-oil emulsion cosmetics (cream) of the blending compositions shown in Table 2 below by blending bis-diglyceryl polyacyladipate-2 and using various kinds of additional oils in combination. Then, each sample was evaluated for the evaluation items (2) to (6) in the above-described evaluation criteria. The results are shown in Table 2.

TABLE 2

|  | Compatibility | Property | Test Example 2-1 | Test Example 2-2 | Test Example 2-3 | Test Example 2-4 |
| --- | --- | --- | --- | --- | --- | --- |
| Bis-diglyceryl polyacyladipate-2 |  |  | 5 | 5 | 5 | 5 |
| Decamethyltetrasiloxane | X | volatile | 20 | — | — | — |
| Isohexadecane | ○ | volatile | — | 20 | — | — |
| Dimethylpolysiloxane | X | non-volatile | — | — | 20 | — |
| Squalane | ○ | non-volatile | — | — | — | 20 |
| Dimethyl distearyl ammonium modified hectorite |  |  | 1.7 | 1.7 | 1.7 | 1.7 |
| Polyoxyethylene/methylpolysiloxane copolymer |  |  | 0.5 | 0.5 | 1.5 | 0.5 |
| Ion-exchanged water |  |  | balance | balance | balance | balance |
| Glycerin |  |  | 8 | 8 | 8 | 8 |
| Sodium chloride |  |  | 0.5 | 0.5 | 0.5 | 0.5 |
| Evaluation (2): Resilient and supple feels |  |  | A* | B | B | C |
| Evaluation (3): Stability |  |  | A | A | A | A |
| Evaluation (4): Elastic feeling |  |  | B | B | A | A |
| Evaluation (5): Softness |  |  | B | B | A | A |
| Evaluation (6): Moisturizing effect |  |  | B | B | A | A |

According to Table 2, the resilient and supple feels were excellent in Test Example 2-1, wherein bis-diglyceryl polyacyladipate-2 and a volatile oil of low compatibility with bis-diglyceryl polyacyladipate-2 were blended. If we compare this with Test Example 1-4, it is clear that the stability was improved by existing as a water-in-oil emulsion cosmetic. Thus, it is suggested that the bis-diglyceryl polyacyladipate-2 in the oil phase is stably dispersed, without separation (precipitation), in the continuous-phase additional oil by existing as a water-in-oil emulsion system.

On the other hand, the water-in-oil emulsion cosmetic, wherein a volatile oil highly compatible with bis-diglyceryl polyacyladipate-2 (Test Example 2-2) or a non-volatile oil of low compatibility with bis-diglyceryl polyacyladipate-2 (Test Examples 2-3 and 2-4) was added in addition to bis-diglyceryl polyacyladipate-2, was not satisfactory in the resilient and supple feels.

Thus, it was found that a stable cosmetic can be obtained without losing a resilient and supple feels due to bis-diglyceryl polyacyladipate-2 when a water-in-oil emulsion cosmetic is made by blending (A) bis-diglyceryl polyacyladipate-2 and (B) (b1) a volatile oil of low compatibility with bis-diglyceryl polyacyladipate-2 with (C) an emulsifying agent and (D) an aqueous component.

As a result of further investigation by the present inventors, when the blending quantity of decamethyltetrasiloxane was increased to 40 mass % in Test Example 2-1, the separation of bis-diglyceryl polyacyladipate-2 was observed over time, and the evaluation turned out to be "C" in evaluation item (3). Therefore, in the water-in-oil emulsion cosmetic of the present invention, the blending quantity of (D) the aqueous component is necessary to be 60 mass % or higher.

Subsequently, other components effective for the further improvement in stability and the feeling in use were investigated. The present inventors prepared each water-in-oil emulsion cosmetic (cream) with the blending composition shown in Table 3 in a normal method. Then, each sample was evaluated for the evaluation items (2) to (6) in the above-described evaluation criteria. The results are shown in Table 3.

TABLE 3

|   |   |   | Test Example | | | | | | |
|---|---|---|---|---|---|---|---|---|---|
|   |   |   | 3-1 | 3-2 | 2-1 | 3-3 | 3-4 | 3-5 | 3-6 |
| (A) |   | Bis-diglyceryl polyacyladipate-2 | 2 | 2 | 5 | 5 | 5 | 5 | 5 |
| (B) | (b1) | Decamethyltetrasiloxane | 19.5 | 18 | 20 | 17 | 14 | 9 | 5 |
|   |   | Squalane | 0.5 | 2 | — | 3 | 6 | 11 | 15 |
| (C) |   | Dimethyl distearyl ammonium modified hectorite | 1.7 | 1.7 | 1.7 | 1.7 | 1.7 | 1.7 | 1.7 |
|   |   | Polyoxyethylene/ methylpolysiloxane copolymer | 0.5 | 0.5 | 0.5 | 0.5 | 0.5 | 0.5 | 0.5 |
| (D) |   | Ion-exchanged water | balance | balance | balance | balance | balance | balance | balance |
|   |   | Glycerin | 8 | 8 | 8 | 8 | 8 | 8 | 8 |
|   |   | Sodium chloride | 0.5 | 0.5 | 0.5 | 0.5 | 0.5 | 0.5 | 0.5 |
| Blending quantity of (A) + (B) | | | 22 | 22 | 25 | 25 | 25 | 25 | 25 |
| Blending quantity of (b1)/ Blending quantity of (A) + (B) | | | 89 | 82 | 80 | 68 | 56 | 36 | 20 |
| Evaluation (2): Resilient and supple feels | | | A* | A* | A* | A* | A | B | C |
| Evaluation (3): Stability | | | A | A | A | A | A* | A* | A* |
| Evaluation (4): Elastic feeling | | | B | A | B | A | A | A | A |
| Evaluation (5): Softness | | | B | A | B | A | A | A | A |
| Evaluation (6): Moisturizing effect | | | B | A | B | A | A | A | A |

According to Test Examples 3-2 to 3-4, wherein squalane was blended into the sample of Test Example 2-1 containing suitably blended components (A) to (D), the stability and the feeling in use are found to be improved because of the blending of these oils.

As a result of further investigation by the present inventors, the oils represented by squalane, which are effective for the improvement of stability and the feeling in use, were found to have a viscosity less than 1000 mPa·s.

Moreover, the resilient and supple feels and the feeling in use are affected by the percentage of (b1) a volatile oil of low compatibility with bis-diglyceryl polyacyladipate-2 with respect to component (A) and component (B).

Accordingly, in the water-in-oil emulsion cosmetic of the present invention, (b2) an oil whose viscosity is less than 1000 mPa·s is preferably contained.

Moreover, it is necessary that the percentage of component (b1), the volatile oil of low compatibility with bis-diglyceryl polyacyladipate-2, is 40 to 85% with respect to component (A) and component (B).

Subsequently, the blending quantity of each oil was investigated. The present inventors prepared each water-in-oil emulsion cosmetic (cream) with the blending composition shown in Table 4 blending varied the blending quantity of several oils in a normal method. Then, each sample was evaluated for the evaluation items (2) to (6) in the above-described evaluation criteria. The results are shown in Table 4.

TABLE 4

|   |   |   | Test Example | | | |
|---|---|---|---|---|---|---|
|   |   |   | 4-1 | 4-2 | 4-3 | 4-4 |
| (A) |   | Bis-diglyceryl polyacyladipate-2 | 5 | 2 | 2 | 5 |
| (B) | (b1) | Decamethyl-tetrasiloxane | 14 | 12 | 12 | 17 |
|   | (b2) | Squalane | 6 | 5 | 4 | 6 |
| (C) |   | Dimethyl distearyl ammonium modified hectorite | 1.7 | 1.7 | 1.7 | 1.7 |
|   |   | Polyoxyethylene/ methylpolysiloxane copolymer | 0.5 | 0.5 | 0.5 | 0.5 |

TABLE 4-continued

|   |   |   | Test Example | | | |
|---|---|---|---|---|---|---|
|   |   |   | 4-1 | 4-2 | 4-3 | 4-4 |
| (D) |   | Ion-exchanged water | balance | balance | balance | balance |
|   |   | Glycerin | 8 | 8 | 8 | 8 |
|   |   | Sodium chloride | 0.5 | 0.5 | 0.5 | 0.5 |
| Blending quantity of (A) + (B) | | | 25 | 19 | 18 | 28 |
| Blending quantity of (b1)/ Blending quantity of (A) + (B) | | | 56 | 63 | 67 | 61 |
| Evaluation (2): Resilient and supple feels | | | A | B | A | A |
| Evaluation (3): Stability | | | A* | A* | A* | A* |
| Evaluation (4): Elastic feeling | | | A | A | A | A |
| Evaluation (5): Softness | | | A | A | A | A |
| Evaluation (6): Moisturizing effect | | | A | A | A | A |

According to Table 4, even when the percentage of (b1) a volatile oil of low compatibility with bis-diglyceryl polyacyladipate-2 in the total oil satisfies 40 to 85%, the resilient and supple feels were somewhat poor in Test Example 4-2, wherein the blending quantity of component (b2) is more than two times of the blending quantity of component (A).

Accordingly, the blending quantity of component (b2) is preferably two times or less of the blending quantity of component (A).

Subsequently, the emulsion type was investigated. The present inventors prepared each water-in-oil emulsion cosmetic (cream) with the blending composition shown in Table 5 blending varied emulsifying agents in a normal method. The present inventors also prepared an oil-in-water emulsion cosmetic of below-described Test Example 5-5 in a normal method. Then, each sample was evaluated for the evaluation items (2) to (6) in the above-described evaluation criteria. The results are shown in Table 5.

TABLE 5

|  |  |  | Test Example | | | | |
| --- | --- | --- | --- | --- | --- | --- | --- |
|  |  |  | 5-1 | 5-2 | 5-3 | 5-4 | 5-5 |
| (A) |  | Bis-diglyceryl polyacyladipate-2 | 5 | 5 | 5 | 5 | 5 |
| (B) | (b1) | Decamethyltetrasiloxane | 20 | 20 | 15 | 15 | 20 |
| (C) |  | Dimethyl distearyl ammonium modified hectorite | 1.7 | — | — | — | — |
|  |  | Polyoxyethylene/methylpolysiloxane copolymer | 0.5 | — | 0.9 | — | — |
|  |  | Alkyl/polyether modified silicone | — | 2 | — | — | — |
|  |  | Cross-linked polyether modified silicone/methyl polysiloxane mixture | — | — | 3 | — | — |
|  |  | Poly(oxyethylene/oxypropylene) methylpolysiloxane copolymer | — | — | — | 1.3 | — |
|  |  | PEG-60 glyceryl isostearate | — | — | — | — | 1.8 |
|  |  | Glyceryl monostearate | — | — | — | — | 1.7 |
|  |  | Propylene glycol monostearate (self-emulsification type) | — | — | — | — | 0.5 |
| (D) |  | Ion-exchanged water | balance | balance | balance | balance | balance |
|  |  | Glycerin | 8 | 8 | 8 | 8 | 8 |
|  |  | Sodium chloride | 0.5 | 1 | 1 | 1 | — |
|  |  | Phenoxyethanol | 0.5 | 0.5 | 0.5 | 0.5 | — |
|  |  | Ethanol | — | 3 | 7 | 7 | — |
| Blending quantity of (A) + (B) | | | 25 | 25 | 25 | 25 | 20 |
| Blending quantity of (b1)/Blending quantity of (A) + (B) | | | 80 | 80 | 60 | 60 | 20 |
| Emulsion type | | | W/O | W/O | W/O | W/O | O/W |
| Evaluation (2): Resilient and supple feels | | | A* | A* | A* | A* | C |
| Evaluation (3): Stability | | | A | A | A | A | A |
| Evaluation (4): Elastic feeling | | | B | A | B | B | A |
| Evaluation (5): Softness | | | B | A | B | B | A |
| Evaluation (6): Moisturizing effect | | | B | A | B | B | A |

According to Test Examples 5-1 to 5-4, various kinds of (C) emulsifying agents can be used in the water-in-oil emulsion cosmetic of the present invention.

However, in Test Example 5-5 wherein the emulsion cosmetic was of oil-in-water type, the resilient and supple feels were poor.

Accordingly, it is necessary that the emulsion cosmetic of the present invention comprising the components (A) to (D) is a water-in-oil emulsion.

Hereinafter, formulation examples of the water-in-oil emulsion cosmetic of the present invention will be illustrated. It is to be understood that the present invention is not limited by these formulation examples.

Formulation Example 1

Cream

| (1) Glycerin | 5 mass % |
| --- | --- |
| (2) Sodium chloride | 0.5 |
| (3) Water | balance |
| (4) Distearyldimonium hectorite | 1.7 |
| (5) Polyoxyethylene/methylpolysiloxane copolymer | 0.5 |
| (6) Decamethyltetrasiloxane | 10 |
| (7) Squalane | 2 |
| (8) Cetyl ethylhexanoate | 2 |
| (9) Vaseline | 0.5 |
| (10) Bis-diglyceryl polyacyladipate-2 | 2.5 |

Blending quantity of (b1)/blending quantity of (A) + (B): 58.8%

(Process)

Components (4) to (10) were mixed with heating; thus uniform dispersion was carried out for the oil phase. A water phase containing (1) to (3) is mixed. The heated water phase was gradually added to the oil phase, and emulsion particles were prepared, after uniformly dispersing with a homodisper, and cooled with stirring; thus a cream that is a water-in-oil emulsion cosmetic was produced. The stability of the obtained water-in-oil cream was good, and it had an excellent use feeling in resilient and supple feels.

Formulation Example 2

Cream

| (1) Glycerin | 5 mass % |
| --- | --- |
| (2) Sodium chloride | 0.5 |
| (3) Water | balance |
| (4) Distearyldimonium hectorite | 2 |
| (5) Polyoxyethylene/methylpolysiloxane copolymer | 1 |
| (6) Decamethylpentasiloxane | 15 |
| (7) Squalane | 6 |
| (8) Glyceryl triethylhexanoate | 5 |
| (9) Bis-diglyceryl polyacyladipate-2 | 10 |

Blending quantity of (b1)/blending quantity of (A) + (B): 41.7%

(Process)

Components (4) to (9) were mixed with heating; thus uniform dispersion was carried out for the oil phase. A water phase containing (1) to (3) is mixed. The heated water phase was gradually added to the oil phase, and emulsion particles were prepared, after uniformly dispersing with a homodisper, and cooled with stirring; thus a cream that is a water-in-oil emulsion cosmetic was produced. The stability of the obtained water-in-oil cream was good, and it had an excellent use feeling in resilient and supple feels.

Formulation Example 3

Cream

| | | |
|---|---|---|
| (1) | Glycerin | 5 mass % |
| (2) | Sodium chloride | 0.5 |
| (3) | Water | balance |
| (4) | Distearyldimonium hectorite | 2 |
| (5) | Polyoxyethylene/methylpolysiloxane copolymer | 1 |
| (6) | Decamethyltetrasiloxane | 13 |
| (7) | Liquid paraffin | 4 |
| (8) | Methylphenylpolysiloxane | 2 |
| (9) | Hydrogenated polyisobutene | 1 |
| (10) | Bis-diglyceryl polyacyladipate-2 | 4 |

Blending quantity of (b1)/blending quantity of (A) + (B): 54.2%

(Process)

Components (4) to (10) were mixed with heating; thus uniform dispersion was carried out for the oil phase. A water phase containing (1) to (3) is mixed. The heated water phase was gradually added to the oil phase, and emulsion particles were prepared, after uniformly dispersing with a homodisper, and cooled with stirring; thus a cream that is a water-in-oil emulsion cosmetic was produced. The stability of the obtained water-in-oil cream was good, and it had an excellent use feeling in resilient and supple feels.

DESCRIPTION OF THE NUMERALS

1: (A) Bis-diglyceryl polyacyladipate-2
2: An additional oil
3: A skin

| DESCRIPTION OF THE NUMERALS | |
|---|---|
| 1: | (A) Bis-diglyceryl polyacyladipate-2 |
| 2: | An additional oil |
| 3: | A skin |

What is claimed is:

1. A water-in-oil emulsion cosmetic comprising the following (A) to (D):
   (A) 0.5 to 10 mass % of bis-diglyceryl polyacyladipate-2
   (B) an oil containing (b1)
   (b1) a volatile oil of low compatibility with (A), wherein said volatile oil does not form a transparent uniform layer with (A)
   (C) an emulsifying agent
   and (D) 60 to 90 mass % of an aqueous component,
   wherein the percentage of component (b1) is 40 to 85% with respect to component (A) and component (B).

2. The water-in-oil emulsion cosmetic according to claim 1, wherein component (B) further contains (b2), an oil with a viscosity less than 1000 mPa·s, and the blending quantity of component (b2) is two times or less of the blending quantity of component (A).

* * * * *